(12) United States Patent
Ahn et al.

(10) Patent No.: US 10,211,382 B2
(45) Date of Patent: Feb. 19, 2019

(54) LED CHIP INTEGRATED WITH HYBRID SENSOR AND METHOD OF FABRICATING THE SAME

(71) Applicant: Pukyong National University Industry-University Cooperation Foundation, Busan (KR)

(72) Inventors: Hyung Soo Ahn, Busan (KR); Sam Nyung Yi, Busan (KR); Min Yang, Busan (KR); Kee Sam Shin, Busan (KR); Young Moon Yu, Seoul (KR)

(73) Assignee: PUKYONG NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 0 days.

(21) Appl. No.: 15/648,825

(22) Filed: Jul. 13, 2017

(65) Prior Publication Data
US 2017/0317254 A1    Nov. 2, 2017

Related U.S. Application Data

(62) Division of application No. 14/654,102, filed as application No. PCT/KR2015/002832 on Mar. 23, 2015, now Pat. No. 9,831,405.

(30) Foreign Application Priority Data

May 9, 2014   (KR) .................. 10-2014-0055844
Dec. 2, 2014   (KR) .................. 10-2014-0170126

(51) Int. Cl.
*H01L 33/62* (2010.01)
*G01N 27/12* (2006.01)
*H01L 27/15* (2006.01)
*G01N 27/403* (2006.01)
*H01L 33/06* (2010.01)
*H01L 33/36* (2010.01)
(Continued)

(52) U.S. Cl.
CPC ............. *H01L 33/62* (2013.01); *G01N 27/12* (2013.01); *G01N 27/403* (2013.01); *H01L 27/15* (2013.01); *H01L 33/007* (2013.01); *H01L 33/06* (2013.01); *H01L 33/32* (2013.01); *H01L 33/36* (2013.01)

(58) Field of Classification Search
CPC ...... G01N 27/12; G01N 27/403; H01L 33/06; H01L 33/62
See application file for complete search history.

(56) References Cited

U.S. PATENT DOCUMENTS 6,997,040 B1    2/2006   Lee
2002/0139987 A1*  10/2002   Collins, III ........... H01L 27/153
                                          257/88
(Continued)

*Primary Examiner* — Marcos D. Pizarro
*Assistant Examiner* — Antonio Crite
(74) *Attorney, Agent, or Firm* — Dilworth & Barrese, LLP.; Michael J. Musella, Esq.

(57) ABSTRACT

The present invention relates to a light emitting diode (LED) chip, in which a hybrid sensor is formed in a nitride-based LED structure. A chip structure embedded with such a hybrid sensor functions as an LED light emitting sensor which can monitor environmental pollution while functioning as a lighting element at the same time and has an effect of being used as a variety of environment pollution sensors according to the type of an electrode material.

4 Claims, 11 Drawing Sheets

(51) Int. Cl.
*H01L 33/00* (2010.01)
*H01L 33/32* (2010.01)

(56) References Cited

U.S. PATENT DOCUMENTS

2014/0009295 A1 1/2014 Kim
2015/0020577 A1 1/2015 Luebke

* cited by examiner

[Fig. 1]
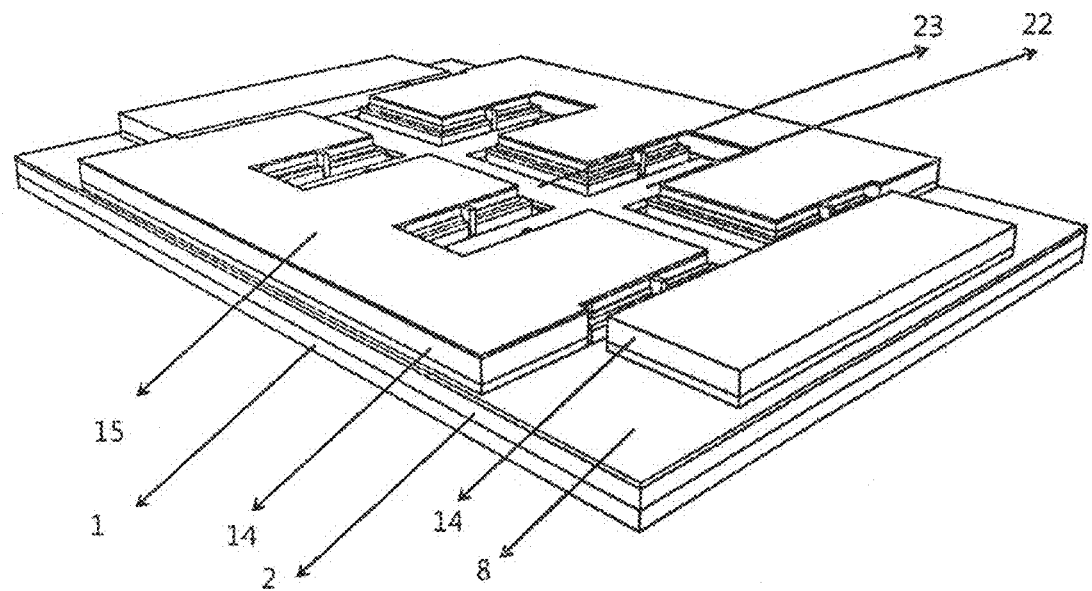
[Fig. 2]
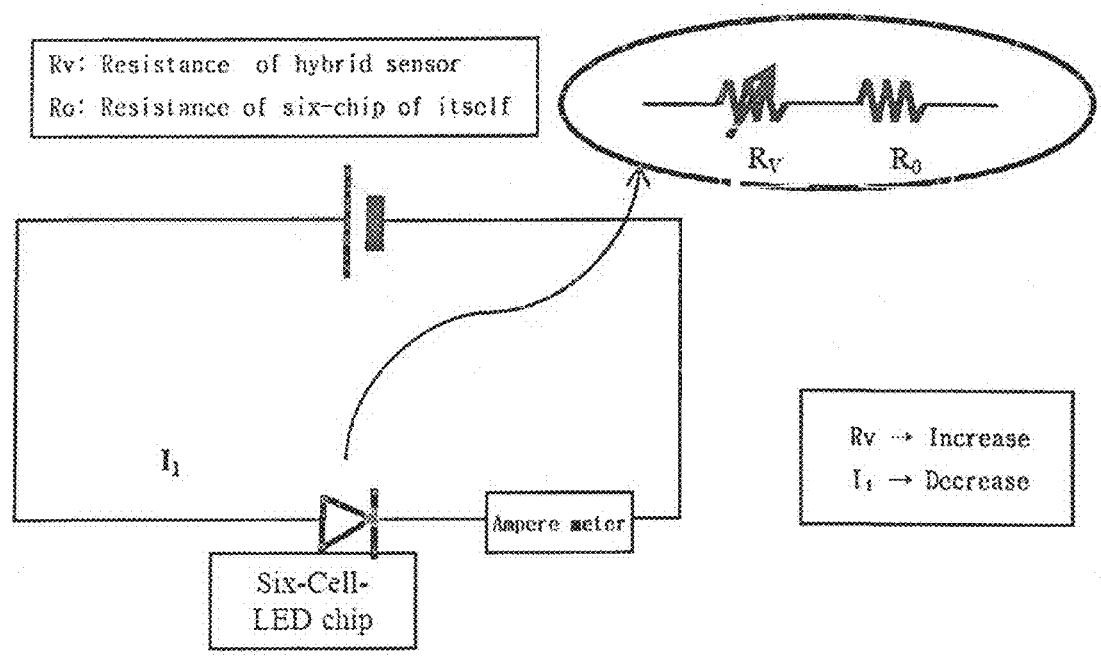

[Fig. 3]
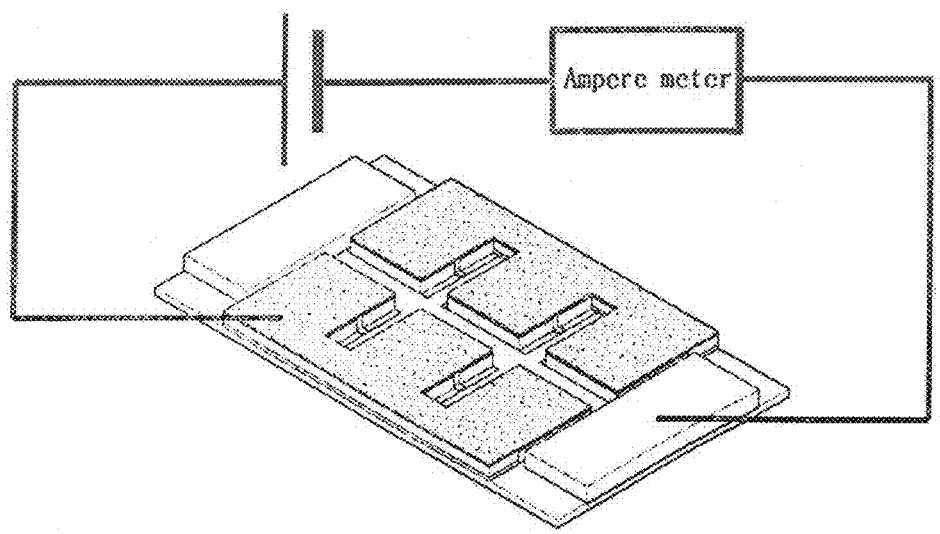
[Fig. 4]
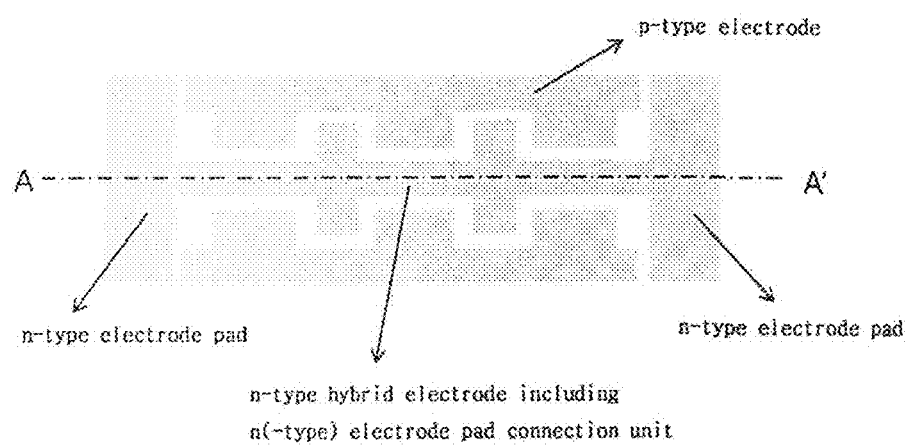

[Fig. 5]
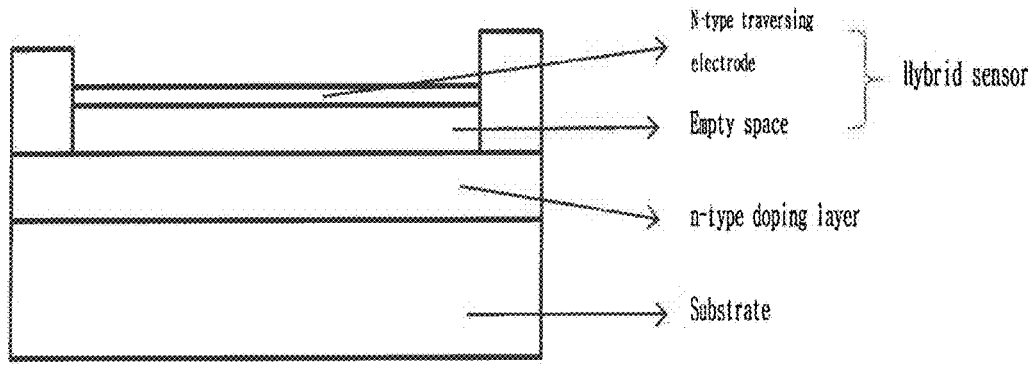
[Fig. 6]
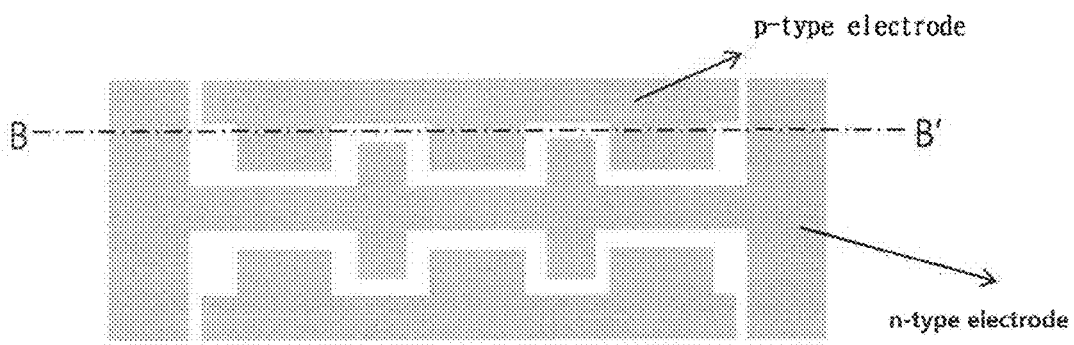
[Fig. 7]
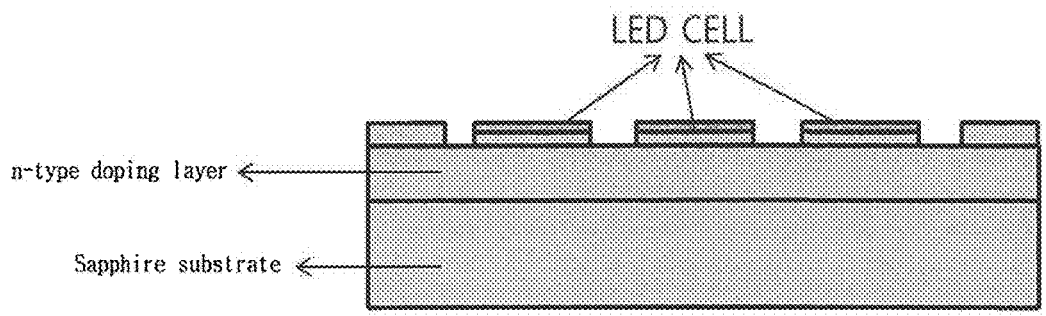

[Fig. 8]
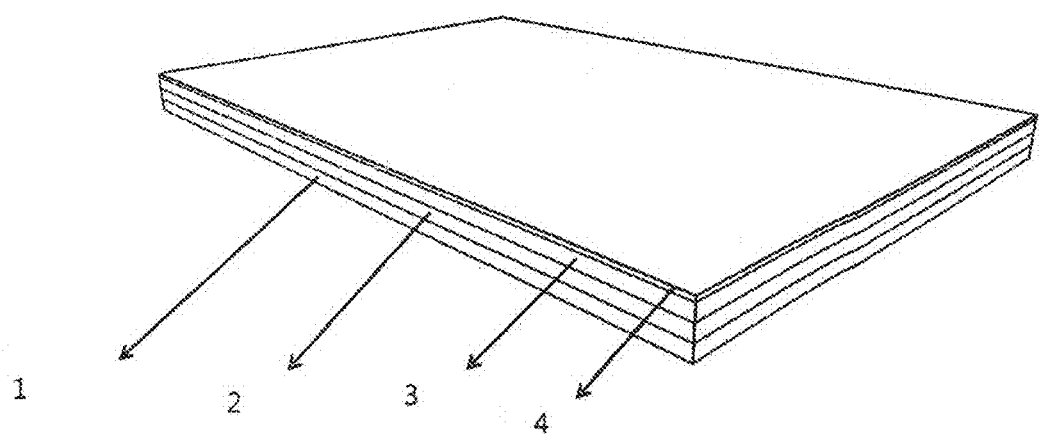
1    2    3    4
[Fig. 9]
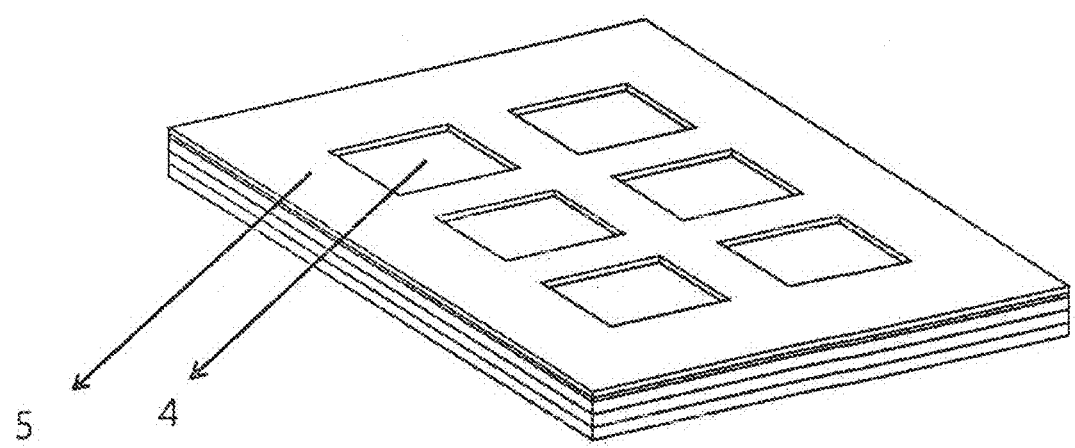
5    4

[Fig. 10]
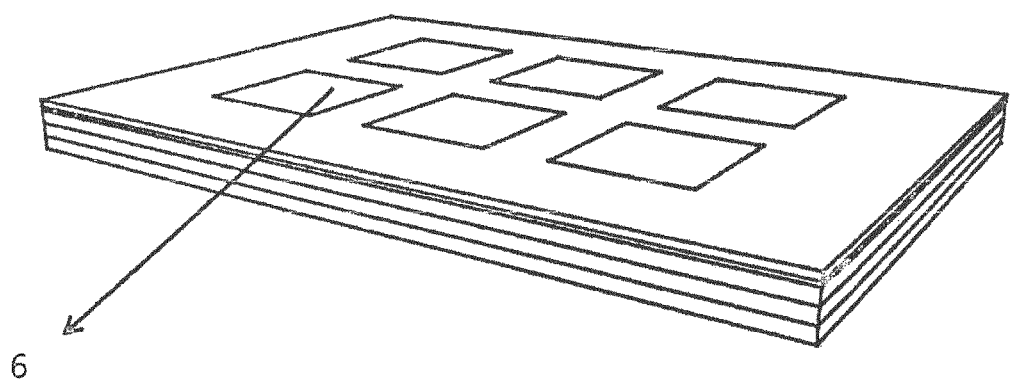
6
[Fig. 11]
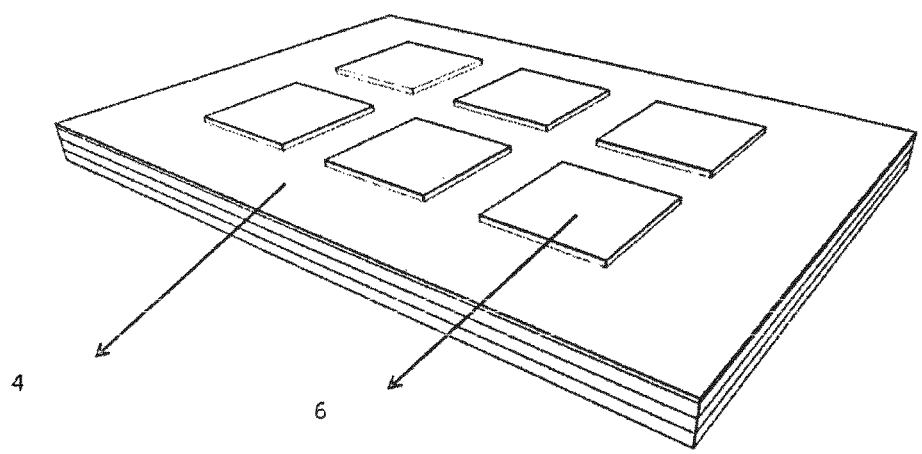
4        6

[Fig. 12]
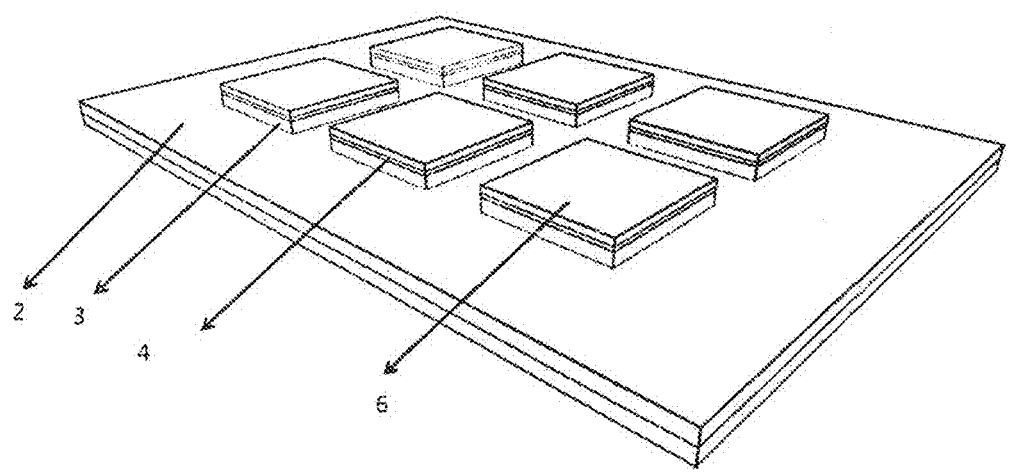
[Fig. 13]
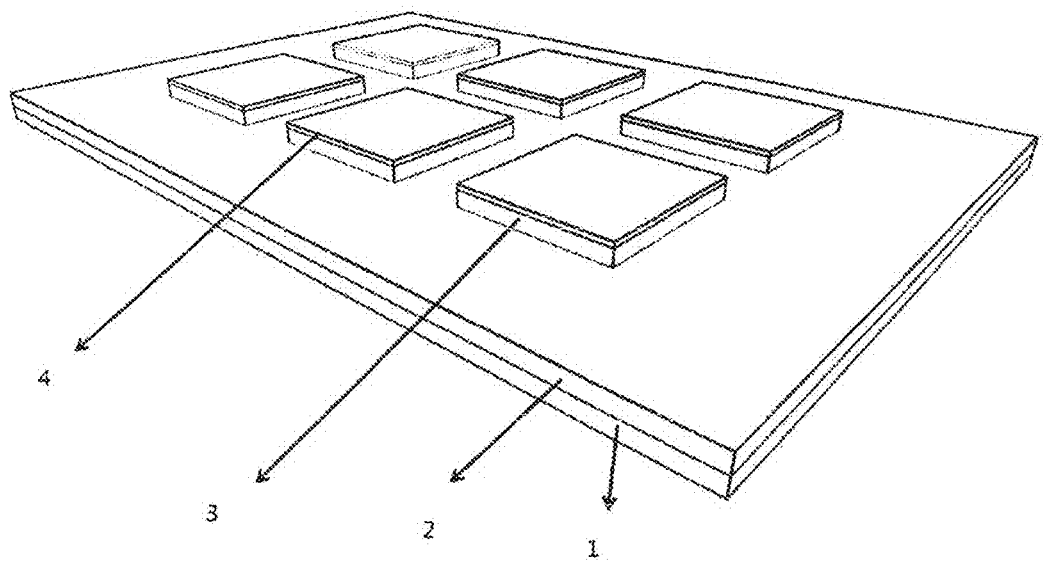

[Fig. 14]
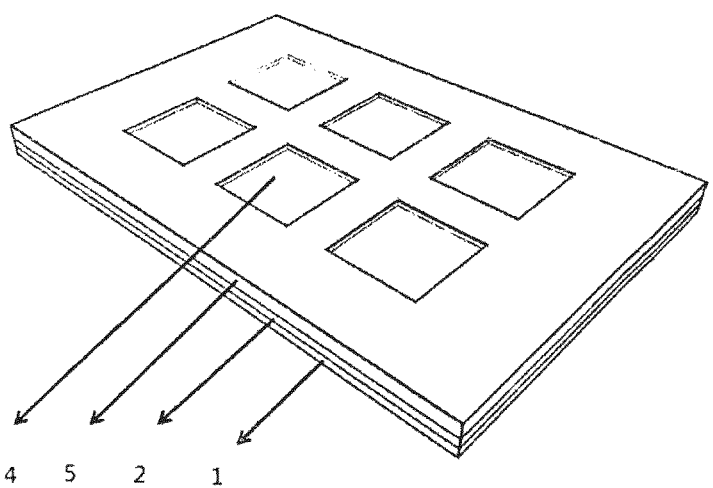
4　5　2　1
[Fig. 15]
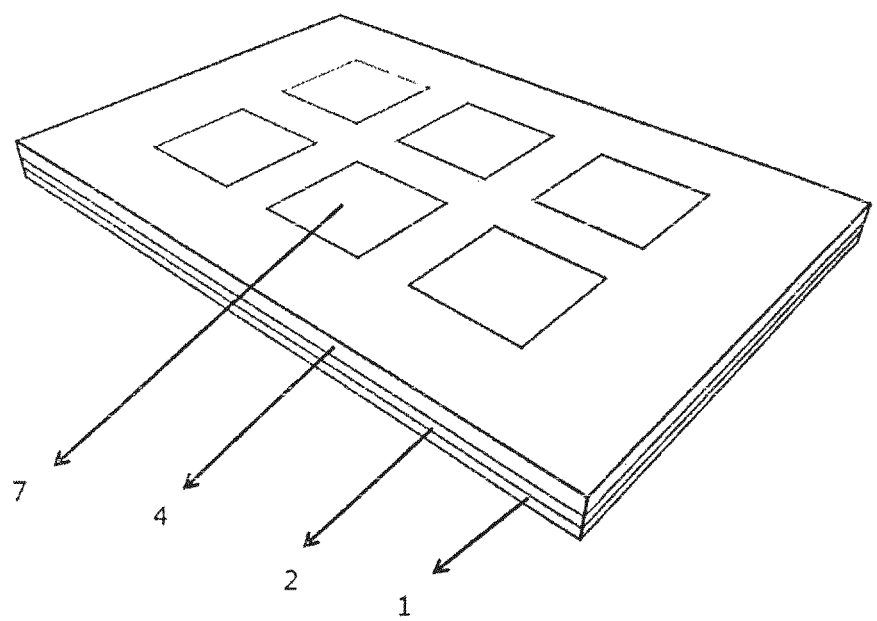
7　4　2　1

[Fig. 16]
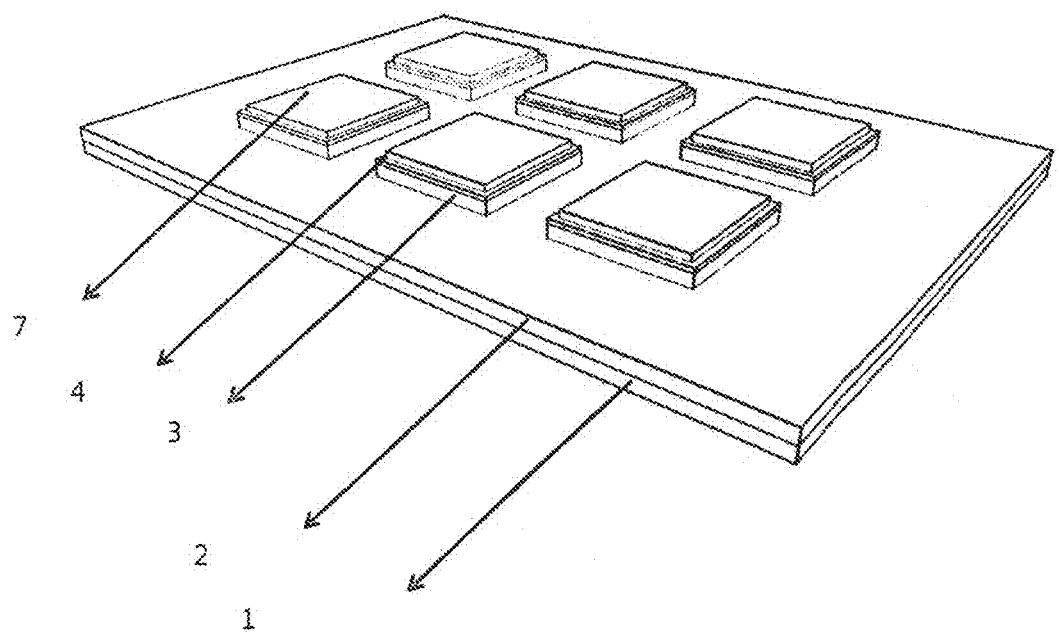
[Fig. 17]
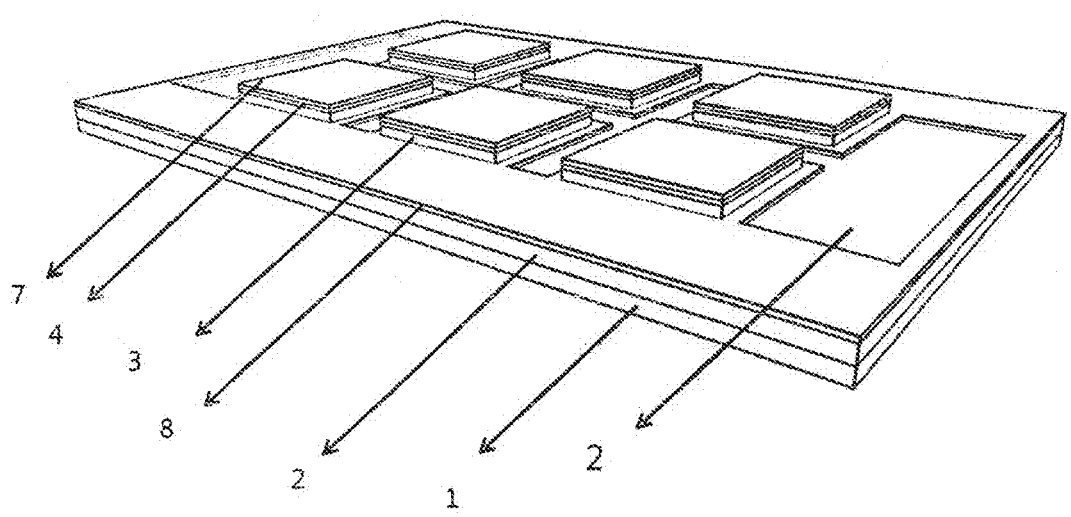

[Fig. 18]
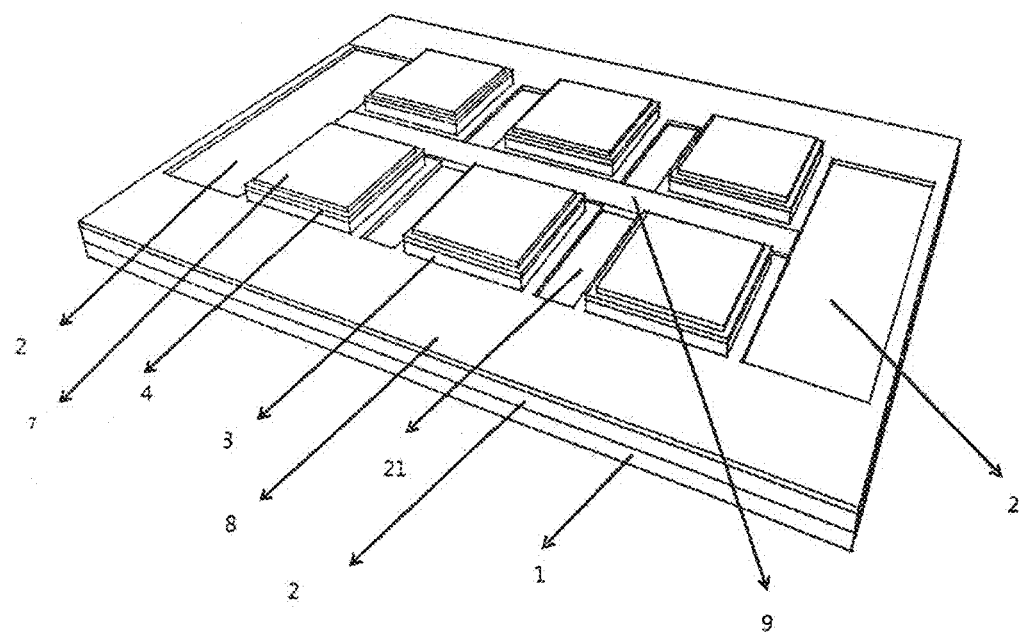
[Fig. 19]
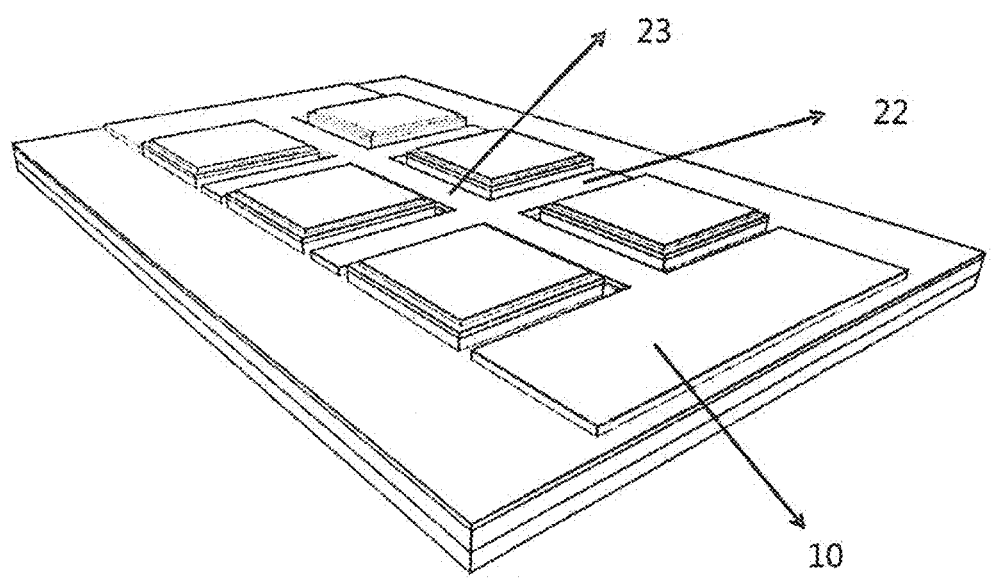

[Fig. 20]
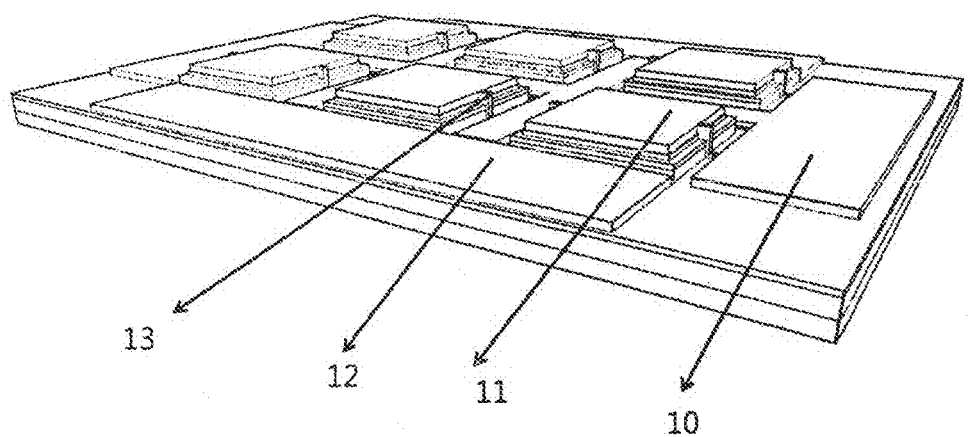
13  12  11  10
[Fig. 21]
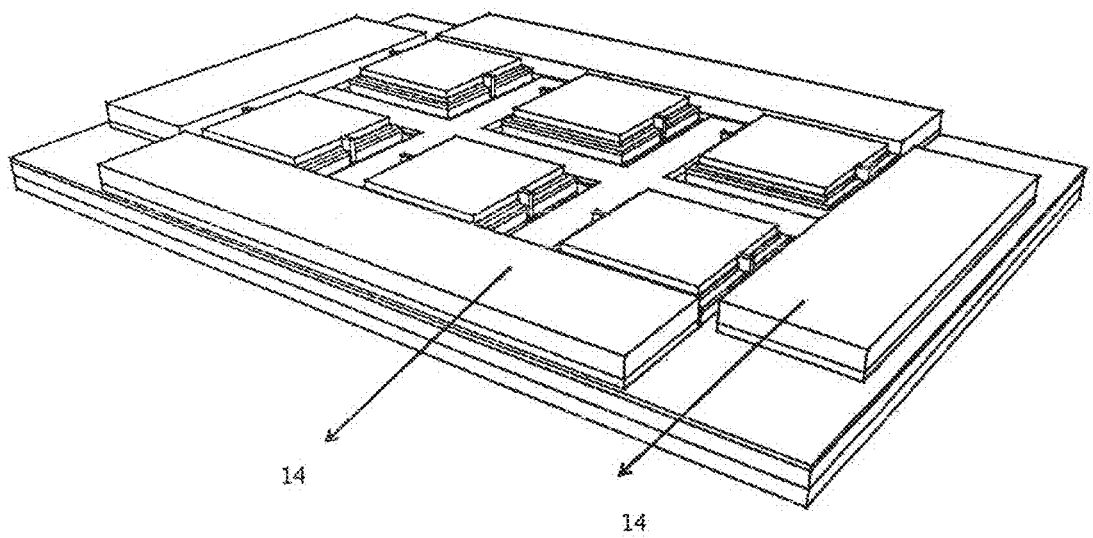
14  14

[Fig. 22]
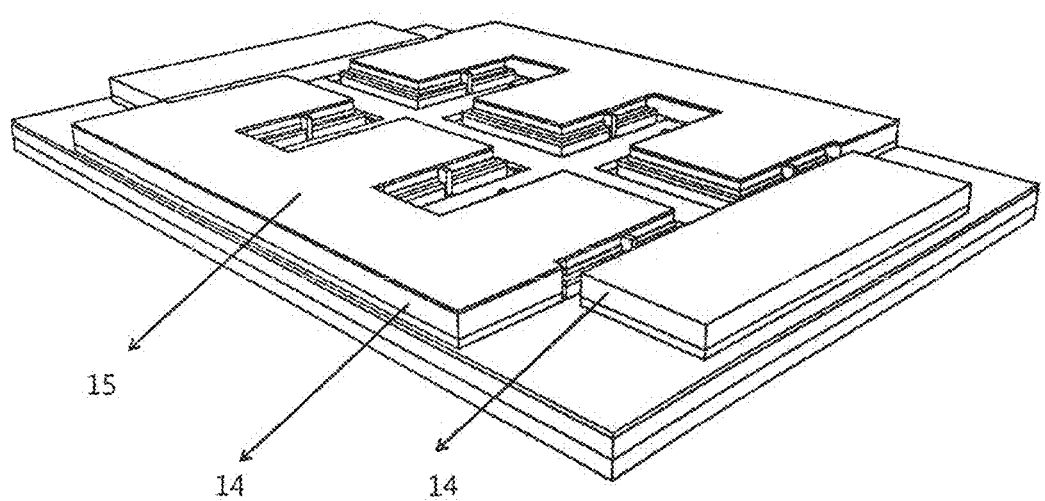

LED CHIP INTEGRATED WITH HYBRID SENSOR AND METHOD OF FABRICATING THE SAME

This application is divisional application of U.S. application Ser. No. 14/654,102, filed Jun. 19, 2015, which claims benefit to International Application No. PCT/KR2015/002832, filed Mar. 23, 2015, which claims priority to Korean Application No. 10-2014-0055844, filed May 9, 2014, and Korean Application No. 10-2014-0170126, filed Dec. 2, 2014, the entire contents of each of which are incorporated herein by reference.

TECHNICAL FIELD

The present invention relates to a light emitting diode (LED) chip, in which a hybrid sensor is formed in a nitride-based LED structure.

BACKGROUND ART

One of important roles of a sensor is detecting various chemicals or materials originating from living creatures, such as concentration of a variety of ions, concentration of gases such as oxygen or carbon dioxide and the like. In order to monitor water pollution, air pollution and the like which may occur in our surrounding environment, sensors capable of measuring various gases such as CO, COx and the like, ions and humidity are frequently used. In the case of gas sensors, numerous sensors haven been developed starting from the catalytic combustion type sensor of Johnson introduced in 1923. In the case of semiconductor gas sensors, they can be largely divided into resistive type sensors and non-resistive type sensors, and the semiconductor gas sensor is a very useful since it may detect various kinds of gases.

As high-tech elements with superior performance have been developed using a material such as polymer, semiconductor, ceramic or the like, humidity sensors are also developed in the form of converting humidity into electric signals and, specifically, a sensor for converting humidity and outputting impedance, electrical conductivity, thermal conductance, electrostatic capacitance or the like.

A method of measuring humidity is divided into a direct measurement method and an indirect measurement method. The direct measurement method includes various hygrometers based on a saturation, absorption or evaporation method. The indirect measurement method includes a method of evaluating moisture adsorption or spectroscopic characteristics, and measurements of electrical conductivity, surface conductivity, change of dielectric constant, near infrared absorption, pressure difference by diffusion speed, change of ionization potential and the like correspond thereto.

Although LEDs are widely used in the present and gradually extending their application fields in a specific area related to illumination, a function as a sensor is performed by individual sensors irrelevant to the LEDs as described above. Accordingly, a sensor formed in a structure integrated with an LED cannot be found in the prior art, and, particularly, an LED sensor for measuring a specific pollutant or measuring temperature or pressure in such a structure and informing a degree of pollution does not exist now.

DISCLOSURE OF INVENTION

Technical Problem

Therefore, the present invention has been made to provide a nitride-based Light Emitting Diode (LED), which can be used to determine whether or not a surrounding environment is polluted with sensing a pollution level of the surrounding environment while light emission of the LED operating as a lighting element is continued.

Technical Solution

According to one aspect of the present invention, there is provided an LED chip integrated with a hybrid sensor, the LED chip including: a sapphire substrate; an n-type semiconductor layer formed on the substrate; two or more LED cells formed on the n-type semiconductor layer; a p-type electrode formed on a p-type semiconductor layer of the LED cells, and a p-type electrode pad formed on an insulation layer, which is formed on the n-type semiconductor layer, by extending the p-type electrode; n-type electrode pads facing each other and formed on a portion of the n-type semiconductor layer exposed in an area where the insulation layer is removed by etching; an n-type pad-to-pad electrode passing through a central portion while connecting the n-type electrode pads on both sides; and an empty space formed under the n-type pad-to-pad electrode (n-type electrode pad connection unit or hybrid electrode).

The LED chip of the present invention may include an output device connected to the hybrid sensor having an air gap under the n-type electrode pad connection unit connecting the pad electrodes on both sides. At this point, a device for displaying change of current value can be an output device. In addition, an ampere meter working as a display device may be a device of an analog type or digital type device and may operate in a manner blinking at a value smaller than a predetermined current value or larger than a predetermined current value, and one or more output means different from the aforementioned output device may be applied.

In the LED chip of the present invention, when the hybrid sensor having an empty space under the connection unit connecting the pad electrodes on both sides is damaged by a specific pollutant, the pollution can be sensed since a certain change is delivered to the output device connected to the electrode. The change may be change of current value or increase or decrease of current change rate.

In the LED chip of the present invention, when the hybrid sensor having an empty space under the n-type pad electrode connection unit (n-type hybrid electrode) connecting the n-type electrode pads on both sides is damaged by a specific pollutant, a certain change is delivered to an output device connected thereto, and, at the same time, the LED chip (for example, configured of six cells in the figure) functioning as a lighting element may perform emission of light since flow of current into the underneath semiconductor layer is maintained.

In the LED chip of the present invention, the hybrid sensor including the n-type pad electrode connection unit (n-type hybrid electrode) connecting the pad electrodes on both sides has an empty space under the hybrid sensor. Such an n-type hybrid electrode may include one or more metals (Al, Au, Sn, Ni, Cr and the like) reacting to a chemical gas, such as nerve gas, colorless gas and odorless gas, a specific environment pollution gas (HCl, H2SO4, nitric acid, HF and agua regia), a general environmental pollutant or the like.

The LED chip of the present invention has a space above the n-type electrode pad connection unit since the top of the n-type electrode pad connection unit is lower than the height of the n-type pad electrode or the p-type pad electrode. Since empty spaces are formed above and under the n-type electrode pad connection unit owing to such a configuration, it is helpful to flow air containing pollutants.

According to another aspect of the present invention, there is provided a method of fabricating an LED chip integrated with a hybrid sensor, the method including the steps of: preparing a substrate; stacking a semiconductor layer including an MQW epitaxial layer; forming two or more LED cells; etching silicon oxide of an area in which two or more n-type electrode pads, two or more p-type electrode pads and an n-type traversing electrode are to be formed, after forming an insulation layer, in order to electrically separate an n-type electrode portion from an area corresponding to a p-type electrode; forming a PR pattern of a bridge shape traversing between the LED cells; forming an n-type traversing electrode of a metal bridge shape covering the PR pattern; and removing the PR of a bridge shape.

In the method of fabricating an LED chip, the step of forming the n-type traversing electrode may be a deposition step of forming the metal bridge using a mask.

In the method of fabricating an LED chip, the step of forming the n-type traversing electrode may include a deposition step of forming a metal for the metal bridge; and a photolithography step of forming the deposited metal as a bridge, and the PR of the bridge shape may be removed in the photolithography process.

In the method of fabricating an LED chip, the height of the p-type electrode pad and the n-type electrode pad is set to be higher than the metal bridge.

Advantageous Effects

In the present invention, two or more cells simultaneously emit light by an n-type electrode configured of two or more LED cell structures and two or more n-type pad electrodes formed on an n-type semiconductor layer formed on a substrate and an n-type electrode pad connection unit extended from an n-type electrode pad to connect the n-type electrode pads, a p-type electrode formed on a p-type nitride semiconductor layer, and a p-type pad electrode formed on an insulation layer formed on an n-type semiconductor by extending the p-type pad, and in a chip including such a plurality of light emitting cells, inside of a space under the n-type electrode pad connection unit passing through the center of the chip is formed to be empty. At this point, if n-type electrode is exposed to a surrounding polluted environment for a predetermined period of time, a change may occur in the electrical conductivity, and a degree of pollution and pollutants in the environment can be sensed through the change of current passing through the n-type electrode pad connection unit formed at the center of the chip as the time exposed to the surrounding pollutants is extended. At the same time, although an operating LED generates a minute change in emitting light, it may operate regardless of lifespan. A chip structure embedded with such a hybrid sensor may function as an LED light emitting sensor capable of monitoring environmental pollution and has an effect of being used as diverse environment pollution sensors according to the type of an electrode material.

BRIEF DESCRIPTION OF THE DRAWINGS

FIG. 1 is a view showing a 6-cell LED chip structure embedded with a hybrid sensor which is an embodiment of the present invention.

FIG. 2 is a view showing a circuit diagram including an ampere meter connected to a sensor, in the present invention.

FIG. 3 is a view showing a configuration including an LED element, an ampere meter and a power supply, in the present invention.

FIG. 4 is a top surface view showing a chip including an n-type electrode pad connection unit (an n-type traversing electrode, an electrode between n-type electrode pads or a hybrid electrode: working two way at the same time) and a cutting line A-A'.

FIG. 5 is a cross-sectional view taken along a cross section A-A' of a chip showing an empty space formed under the n-type traversing electrode.

FIG. 6 is a top surface view showing a chip including an n-type traversing electrode and a cutting line B-B'.

FIG. 7 is a cross-sectional view taken along the line B-B' of three cells showing a p-region, an n-region, a light emitting region and an n-type pad electrode.

FIG. 8 is a view showing stack structure including a substrate and an MQW epitaxial layer.

FIG. 9 shows a view when a photolithography step for forming six cells in one chip is finished.

FIG. 10 shows a view when a metal functioning as a dry etching mask is deposited.

FIG. 11 is a view showing a metal mask exposed on the p-type GaN layer.

FIG. 12 shows a view when etching is performed until the n-type GaN layer is exposed.

FIG. 13 shows a view when the metal mask is removed.

FIG. 14 shows a view when a photolithography step for depositing a p-type electrode is finished.

FIG. 15 is a view showing ITO deposited on a p-type layer.

FIG. 16 a view showing ITO remained after lift-off.

FIG. 17 shows a view when silicon oxide is etched in an area where an n-type electrode, a p-type electrode and an n-type traversing electrode are to be formed, after the silicon oxide is deposited.

FIG. 18 is a view showing a state of PR applied before a metal bridge traversing the inside of an element is formed.

FIG. 19 is a view showing a state of forming n-type electrodes and an n-type pad including a metal bridge traversing the inside of an element.

FIG. 20 is a view showing a state of forming a barrier metal and a reflector metal.

FIG. 21 is a view showing a state of forming a primary solder metal on the n-type pad and p-type pad.

FIG. 22 is a view showing a state of forming a secondary solder metal for connecting the p-type pad and the p-type electrode.

| DESCRIPTION OF SYMBOLS | |
|---|---|
| 1: Sapphire substrate | 2: n-GaN |
| 21: n-GaN | |
| 22: n-type electrode pad connection unit | |
| 23: n-type electrode extension unit | |
| 3: MQW | 4: p-GaN |
| 5: PR | 6: Metal (for dry etching mask) |
| 7: ITO | 8: SiO2 |
| 9: PR applied in bridge shape | |
| 10: n-type pad and electrode | 11: Reflector metal |
| 12: Barrier metal | 13: Lightning rod |
| 14: Primary solder | 15: Secondary solder |

BEST MODE FOR CARRYING OUT THE INVENTION

The present invention relates to a nitride-based Light Emitting Diode (LED), in which in a chip having a plurality of light emitting cells, a space under an n-type electrode passing through the center of the chip is formed to be empty so that the LED can sense pollutants while emitting light, through the change of current flowing through the electrode. The LED operating in such a manner has an LED chip structure which does not affect the lifespan of the LED although a minute change may occur in emitting light. That is, the nitride-based Light Emitting Diode (LED) of the present invention relates to a hybrid chip having a structurally embedded sensor together with a general light emitting structure.

FIG. 1 is a view showing a 6-cell LED chip structure embedded with a hybrid sensor, which is an embodiment of the present invention, and the number of cells does not affect the scope of the present invention. An LED chip embedded with a hybrid sensor is shown as an example, and the configuration is as follows. The LED chip includes an n-type semiconductor layer 2 formed on a sapphire substrate 1; six LED cells formed on the semiconductor layer; a hybrid (n-type) electrode 23 passing through the center of the six LED cells; n-type electrode pads formed at both ends of the hybrid (n-type) electrode in some regions of the n-type nitride semiconductor layer exposed by etching an insulation layer; and a p-type electrode pad connected to a p-type electrode formed on a p-type nitride semiconductor layer 4 and configured of solder metals 14 and 15 which covers a barrier metal 12 formed on the insulation layer which is formed on the n-type semiconductor layer.

The circuit diagram of FIG. 2 shows an embodiment of a configuration functioning as a sensor in the present invention. The LED is a 6-cell LED chip having its own hybrid sensor proposed in the present invention, and the hybrid n-type electrode portion functioning as a sensor and also as a negative (−) electrode is expressed as a variable resistor. The 6-cell LED chip embedded with a hybrid sensor according to the present invention is configured not to be changed in the optical output of the LED even when the hybrid (n-type) electrode is completely damaged by pollution.

FIG. 3 is a view showing a configuration including an LED chip as an embodiment of the present invention. The configuration of an electrode is shown in FIGS. 4 to 7 as an embodiment of the present invention. The p-type electrode functions as a positive (+) electrode, and an LED cell structure is included under the p-type electrode as shown in FIG. 7. The n-type hybrid electrode of FIG. 4 functions as a sensor and a negative (−) electrode and may include a layer doped with an n-type doping material as much as ten to the seventeenth power to ten to the nineteenth power. The LED cell structure of FIG. 7 functions as a light emitting region of a general LED.

Referring to FIG. 5, an n-type doping layer is formed on a sapphire substrate. The cross section A-A' of FIG. 4 shows an n-type electrode configured as a hybrid form functioning as a sensor and a negative (−) electrode. With respect to the cross section B-B' of FIG. 6, a cross-sectional view of a cell including an n-region, a p-region and a light emitting region is shown in FIG. 7.

Thickness of the sapphire substrate is about 100 to 250 micrometers, and the dimension of the 6-cell LED can be, for example, 1 mm×1 mm or larger. The hybrid electrode is extended along the left and right direction of the hybrid electrode to act as a common n-type electrode for all the six cells 3 and operates the six LED cells by simultaneously applying a predetermined voltage to the pad metals on both sides of the hybrid electrode along the longitudinal direction. At this point, the hybrid electrode has an empty space separated from the n-type semiconductor layer under a portion connecting the pads at both ends, and the width of the hybrid n-type electrode may have a range of a few tens to a few hundreds of micrometers, and thickness thereof may have a range of 5,000 to 10,000 Armstrong.

In this embodiment, although the p-type electrode is independently formed in each of the six cells and current is individually applied to the p-type electrodes, they are connected through two pad metals. The cells are integrated into two groups by connecting three cells to one pad metal, and each three cells in one group operate together.

The sensor part is a structure having an empty space under the center portion of the hybrid electrode (an n-type hybrid electrode or a hybrid n-type electrode) connecting the pad metals on both sides (FIG. 5). When a voltage is applied for LED operation, resistance and some current are formed in the hybrid electrode connecting the pad metals on both sides, and since the resistance is changed by the change or damage on the hybrid electrode caused by a pollutant and the amount of the flowing current is also changed accordingly, the hybrid electrode functions as a sensor. At this point, the present invention is not influenced by the change of volume of the air gap in the empty space because diffusion by the difference of concentration is the major operating mechanism of propagating chemicals in the form of a fluid state including gas (e.g., air) or the like. That is, although the hybrid electrode part may perform a function of a sensor by sensing a minute change in the current flowing into the hybrid electrode when the hybrid electrode part having an empty space filled with air under the hybrid electrode part is changed and damaged by a pollutant, a function of a lighting element can be performed sufficiently since the operating LED may maintain the flow of current into the n-type doping layer.

Accordingly, the LED chip structure of the present invention having a hybrid sensor therein does not disturb driving an LED which performs a light emitting function and provides an array of nitride-based LEDs having a function capable of sensing a minute degree of pollution in the surrounding environment while the LED is driven to emit light.

A metal type may be configured of a combination of all kinds of metals which can be used as an n-type electrode. For example, it may include Cr/Ni/Au, Ti/Al and the like, and the pollutant may be a hydrochloric material, a sulfonic material, a fluorinated material, high chloride steam, an ammoniac material or the like. For example, if an LED illumination applying an embodiment of the present invention is installed in a sort of equipment or a space (e.g., etching equipment or etch processing section for semiconductor) using a chemical such as hydrochloric acid, it may be utilized in the form of sensing increase of hydrochloric concentration in the air and taking a necessary action when the hydrochloric acid is leaked. Sensitivity of the sensing may be adjusted by the factors such as the types and combination of materials used as an n-type electrode, design of physical dimensions (length, thickness, width, and change of thickness and/or width according to the length) of the electrode and the like. In addition, the display function can be reinforced by computing a current change rate in addition to change of current. That is, the display function may be divided into two or more levels by distinguishing a case where the current is decreased at a high current change rate and a case where the current is decreased at a low current change rate, or the display function may be divided into multi-levels.

FIGS. 8 to 22 show the steps of configuring the present invention. FIG. 8 shows a stack structure of a chip including a substrate and an MQW epitaxial layer, which shows an area of a chip grown on a 2-inch sapphire substrate and cut into pieces of a 6 mm×4 mm size. FIG. 9 shows a view when a photolithography for forming six cells of a 3×2 array in one chip is finished.

FIG. 10 shows view when a metal functioning as a dry etching mask is deposited after the photolithography of forming six cells is finished, FIG. 11 is a view showing a metal mask exposed on the p-type GaN layer which appears after PR is removed. FIG. 12 shows a view when etching is performed until the n-type GaN layer (2) is exposed, other than the portions where the metal for dry etching mask is covered. FIG. 13 shows a state in which the mask metal for dry etching, which is used in forming six cells of a 3×2 array, is removed using hydrofluoric acid.

FIG. 14 shows a view when a photolithography for depositing a p-type electrode is finished. The p-type electrode may be formed as a transparent electrode by using ITO in order to minimize the amount of emitted light which is decreased by the p-type electrode metal. FIG. 15 a view showing ITO deposited on a p-type layer through e-beam evaporation or the like. FIG. 16 shows ITO remained after lift-off. After a lift-off process for removing unnecessary metal parts and PR is progressed using acetone, the ITO remains.

FIG. 17 shows a view when silicon oxide of an area where an n-type electrode, a p-type electrode and an n-type traversing electrode (hybrid electrode) are to be formed is etched to electrically separate the n-type electrode portion from an area corresponding to the p-type electrode, after an insulation layer is formed by depositing and patterning the insulation layer (e.g., SiO2) on the front surface through sputtering or the like. FIG. 18 is a view showing a state of PR applied using a mask only to a metal bridge traversing the inside of an element and a portion of an empty space to be formed under the metal bridge. FIG. 19 is a view showing a state of forming n-type electrodes and an n-type pad including a metal bridge traversing the inside of an element. At this step of forming the structure, the PR 9 applied in the form of a bridge may be removed together in the step of removing PR during the photolithography step of forming the n-type electrodes 22 and 23 and the n-type pad 10. Or, the PR 9 can be removed in a method of progressing each photolithography step for forming the n-type electrode first and a photolithography for forming the n-type pad separately. The empty space can be formed in such a process. In addition, the metal bridge may be formed in the form of a bridge on the PR of a bridge shape using a mask for deposition, and, at this point, the PR at the lower position may be removed by a chemical (e.g., a PR remover or the like) after the metal bridge is formed.

FIG. 20 is a view showing a state of forming a barrier metal 12 for joining metal materials of electrodes; a reflector metal 11 for reflecting light radiated to the p-type electrode toward the substrate; n-type pad-10; and a lightning rod region 13 for preventing damage of elements caused by over current (Korean Patent Registration No. 1011399150000). FIG. 21 is a view showing a state of forming a primary solder metal on the n-type pad and p-type pad in order to remove steps generated when the LED chip is turned over in the form of a flip-chip and the LED chip is adhered to a sub-mount. FIG. 22 is a view showing a state of forming a secondary solder metal for connecting the p-type pad and the p-electrode for smooth flow of current between the p-type pad and the p-electrode. Since height of the pad electrode is leveled through this process, the flip-chip process becomes advantageous, and a height interval with respect to the metal bridge can be secured. As a result, since the metal bridge has empty spaces at the upper and lower portions, polluted air is smoothly diffused, and thus change of pollution can be quickly reflected to the change of current.

The invention claimed is:

1. A method of fabricating an LED chip integrated with a hybrid sensor, the method comprising the steps of:
   preparing a substrate;
   stacking a semiconductor layer including an MQW epitaxial layer on the substrate;
   forming two or more LED cells on the semiconductor layer;
   forming an insulation layer on the LED cells and the substrate;
   patterning the insulation layer to form two or more n-type electrode pads, two or more p-type electrode pads and an n-type traversing electrode;
   etching the insulating layer in order to separate an n-type electrode portion from an area corresponding to a p-type electrode;
   forming a photoresist pattern having a bridge shape traversing between the LED cells;
   forming a connection unit for connecting the n-type electrode pads of a metal bridge shape covering the photoresist pattern of the bridge shape; and
   forming the hybrid sensor by removing the photoresist pattern of the bridge shape.

2. The method according to claim 1, wherein the step of forming a connection unit is a deposition step of forming the metal bridge using a mask.

3. The method according to claim 1, wherein the step of forming a connection unit includes:
   a deposition step of forming a metal for connecting the n-type electrode pads; and
   a photolithography step of forming the deposited metal on the photoresist pattern of the bridge shape in a form of a bridge, wherein the photoresist pattern of the bridge shape is removed in the photolithography process.

4. The method according to claim 1, wherein the height of the p-type electrode pad and the n-type electrode pad is set to be higher than the metal bridge.

* * * * *